(12) United States Patent
Rywak

(10) Patent No.: US 8,026,086 B2
(45) Date of Patent: Sep. 27, 2011

(54) METHODS FOR CO-PRODUCTION OF ETHANOL AND SILICA FROM EQUISETUM

(75) Inventor: Anthony A. Rywak, Burlington (CA)

(73) Assignee: Ontario Inc., Burlington, Ontario ( * ) Notice: Subject to any disclaimer, the term of this patent is extended or adjusted under 35 U.S.C. 154(b) by 596 days.

(21) Appl. No.: 12/051,925

(22) Filed: Mar. 20, 2008

(65) Prior Publication Data

US 2009/0142819 A1 Jun. 4, 2009

Related U.S. Application Data

(60) Provisional application No. 61/005,009, filed on Dec. 3, 2007.

(51) Int. Cl.
C12P 7/06 (2006.01)
C12P 7/03 (2006.01)
(52) U.S. Cl. .................... 435/161; 435/165; 435/168
(58) Field of Classification Search .................. None
See application file for complete search history.

(56) References Cited

U.S. PATENT DOCUMENTS

| | | | |
|---|---|---|---|
| 3,889,608 | A | 6/1975 | Pitt |
| 3,959,007 | A | 5/1976 | Pitt |
| 4,105,459 | A | 8/1978 | Mehta |
| 4,214,920 | A | 7/1980 | Amick et al. |
| 4,247,528 | A | 1/1981 | Dosaj et al. |
| 4,645,605 | A | 2/1987 | Durham |
| 4,676,964 | A | 6/1987 | Seki et al. |
| 5,008,021 | A | 4/1991 | Conner et al. |
| 5,078,795 | A | 1/1992 | Conner et al. |
| 5,782,982 | A | 7/1998 | Farone et al. |
| 5,833,940 | A | 11/1998 | Reiber et al. |
| 5,942,115 | A | 8/1999 | Rieber |
| 6,375,735 | B1 | 4/2002 | Stephens et al. |
| 6,406,678 | B1 | 6/2002 | Shipley |
| 6,524,543 | B1 | 2/2003 | Rieber et al. |
| 6,638,354 | B2 | 10/2003 | Stephens et al. |
| 6,843,974 | B2 | 1/2005 | Kang |
| 7,270,794 | B2 | 9/2007 | Shipley |
| 7,585,652 | B2 * | 9/2009 | Foody et al. .......... 435/163 |
| 7,670,813 | B2 * | 3/2010 | Foody et al. .......... 435/105 |
| 2003/0097966 | A1 | 5/2003 | Stephens et al. |

OTHER PUBLICATIONS

T.E. Timell, Studies on Some Ancient Plants, Svensk Papperstidning, 1964, pp. 356-363, vol. 67, No. 9.
Harold G. Coffin, Vertical Floatation of Horsetails (Equisetum): Geological Implications, Geological Society of America Bulletin, Jul. 1971, pp. 2019-2022, vol. 82.
Prabir K. Basu, C. Judson King and Scott Lynn, Manufacture of Silicon Tetrachloride from Rice Hulls, American Institute of Chemical Engineers Journal, May 1973, pp. 439-445, vol. 19, No. 3.
V.D. Dosaj, L.P. Hunt and A. Schei, High-Purity Silicon for Solar Cell Applications, Journal of Metals, Jun. 1978, pp. 8-13, vol. 6.
J.G. Zeikus, Thermophilic Bacteria: Ecology, Physiology and Technology, Enzyme and Microbial Technology, Oct. 1979, pp. 243-252, vol. 1, issue 4.
J.G. Zeikus, Chemical and Fuel Production by Anaerobic Bacteria, Annual Review of Microbiology, 1980, pp. 423-464, vol. 34.
Thomas K. Ng, Arie Ben-Bassat and J.G. Zeikus, Ethanol Production by Thermophilic Bacteria: Fermentation of Cellulosic Substrates by Cocultures of *Clostridium thermocellum* and *Clostridium thermohydrosulfuricum*, Applied and Environmental Microbiology, Jun. 1981, pp. 1337-1343, vol. 41, No. 6.
James A. Amick, Purification of Rice Hulls as a Source of Solar Grade Silicon for Solar Cells, Journal of the Electrochemical Society: Solid-State Science and Technology, Apr. 1982, pp. 864-866, vol. 129, No. 4.
D.N. Bose, P.A. Govindacharyulu and H.D. Banerjee, Large Grain Polycrystalline Silicon from Rice Husk, Solar Energy Materials, 1982, pp. 319-321, vol. 7.
H.D. Banerjee, S. Sen and H.N. Acharya, Investigations on the Production of Silicon from Rice Husks by the Magnesium Method, Materials Science and Engineering, 1982, pp. 173-179, vol. 52.
Jurgen Wiegel, Ethanol from Cellulose, Experientia, 1982, pp. 151-156, vol. 38, Birkhauser Verlag, Basel, Switzerland.
L.P. Hunt, J.P. Dismukes, J.A. Amick, A. Schei and K. Larsen, Rice Hulls as a Raw Material for Producing Silicon, Journal of the Electrochemical Society: Solid-State Science and Technology, Jul. 1984, pp. 1683-1686, vol. 131, No. 7.
J.A. Amick, J.P. Dismukes, R.W. Francis, L.P. Hunt, P.S. Ravishankar, M. Schneider, K. Matthei, R. Sylvain, K. Larsen and A. Schei, Improved High-Purity Arc-Furnace Silicon for Solar Cells, Journal of the Electrochemical Society: Electrochemical Science and Technology, Feb. 1985, pp. 339-345, vol. 132, No. 2.
Daniel Cloutier and Alan K. Watson, Growth and Regeneration of Field Horsetail (*Equisetum arvense*), Weed Science, 1985, pp. 358-365, vol. 33.
H. Riveros and C. Garza, Rice Husks as a Source of High Purity Silica, Journal of Crystal Growth, 1986, pp. 126-131, vol. 75.

(Continued)

*Primary Examiner* — Herbert J. Lilling
(74) *Attorney, Agent, or Firm* — Bereskin Parr LLP/S.E.N.C.R.L., s.r.l.

(57) ABSTRACT

A method for the co-production of silica and at least one other useful industrial chemical such as ethanol, comprises the steps of: pre-treating siliceous plant matter derived from plants, such as horsetail weeds from the genus *Equisetum*, to create a feedstock having exposed cellulose; placing the feedstock in a reactor containing a biological agent effective to break down the cellulose into at least one useful organic chemical reaction product and a silica-containing co-product; separating the at least one useful organic chemical product from the reactor; separating the silica-containing co-product from the reactor; and refining the silica-containing co-products into silica or other industrially useful silicon containing products. The biological agent may be an anaerobic thermophyllic bacteria, enzymes, or a co-mixture of enzymes and yeast.

22 Claims, 1 Drawing Sheet

OTHER PUBLICATIONS

A. Karera, S. Nargis, S. Patel and M. Patel, Silicon-based Materials from Rice Husk, Journal of Scientific and Industrial Research, Oct. 1986, pp. 441-448, vol. 45.

L.R. Lynd and H.E. Grethlein, Hydrolysis of Dilute Acid Pretreated Mixed Hardwood and Purified Microcrystalline Cellulose by Cell-Free Broth from *Clostridium thermocellum*, Biotechnology and Bioengineering, 1987, pp. 92-100, vol. 29.

Nazma Ikram and M. Akhter, X-Ray Diffraction Analysis of Silicon Prepared from Rice Husk Ash, Journal of Materials Science, 1988, pp. 2379-2381, vol. 23.

M. Patel and P. Kumari, Silicon Carbide from Sugarcane Leaf and Rice Straw, Journal of Materials Science Letters, 1990, pp. 375-376, vol. 9.

G. Holzhuter, K. Narayanan and T. Gerber, Structure of Silica in *Equisetum arvense*, Analytical and Bioanalytical Chemistry, 2003, pp. 512-517, vol. 376.

David B. Levin, Rumana Islam, Nazim Cicek and Richard Sparling, Hydrogen Production by *Clostridium thermocellum* 27405 from Cellulosic Biomass Substrates, International Journal of Hydrogen Energy, 2006, pp. 1496-1503, vol. 31.

Lanny Sapei, Robert Noske, Peter Strauch and Oskar Paris, Isolation of Mesoporous Biogenic Silica from the Perennial Plant *Equisetum hyemale*, Chemistry of Materials, 2008, pp. 2020-2025, vol. 20.

Michael McCoy, Biomass Ethanol Inches fcrward, Efforts to produce ethanol from waste products abound, but sucess is elusive, C&EN Northeast News Bureau, Dec. 7, 1998, pp. 29-32.

\* cited by examiner

METHODS FOR CO-PRODUCTION OF ETHANOL AND SILICA FROM EQUISETUM

RELATED APPLICATIONS

This application claims priority from U.S. application Ser. No. 61/005,009 filed on Dec. 3, 2007.

FIELD OF THE INVENTION

This invention relates to methods for the extraction of silica and other useful industrial chemicals such as ethanol from plant material.

BACKGROUND OF THE INVENTION

There is currently great interest in finding energy sources that are alternatives to petroleum and coal, since we are currently running out of such resources, and perhaps more importantly, because it is becoming increasingly apparent that the burning of these non-carbon-neutral energy sources may be contributing to global climate change.

One area of alternative energy production that has received significant attention is photovoltaics, the conversion of light into electricity, most commonly using silicon based solar cells. Elemental silicon (Si) is produced via the Carbothermic Process, whereby silicon dioxide (typically quartz) is chemically reduced in an electric arc furnace at temperatures in excess of 1400° C. The reducing agents used in this process are carbonaceous, typically coal, charcoal, petroleum coke and wood chips. The net chemical reaction for Si production is:

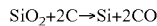

$$SiO_2 + 2C \rightarrow Si + 2CO$$

One major problem with the current art is that, based on the low purity of starting materials, the Si product often contains high levels of undesirable elemental impurities. Such "Metallurgical Grade" (MG) silicon is often only 98% pure, and is entirely unusable in this form for the production of solar cells. One commonly employed method for purifying this MG silicon is to convert it through a high temperature reaction to the low boiling point compound trichlorosilane ($SiHCl_3$), purify this chemical by distillation, then back-convert the $SiHCl_3$ to elemental silicon in the presence of hydrogen gas at temperatures of ca. 1100 to 1200° C., generating HCl gas as a by-product. This purification process is very expensive due to energy requirements, chemical handling requirements, etc. In addition, the cost of the final silicon is approximately 5 to 10 times that which is desired for photovoltaic applications. Furthermore, the purity of the final product far exceeds the requirements for solar-cell manufacture.

A second method for producing photovoltaic (PV) grade silicon is by purifying or "upgrading" MG silicon to a level acceptable for solar-cell manufacture without the need for $SiHCl_3$ as an intermediate. However, two silicon impurities that greatly degrade the performance of solar cells, Boron (B) and Phosphorus (P), cannot readily be removed from silicon using commonly employed methods in the art of silicon purification, such as directional solidification.

Although many novel processes have been devised to selectively remove B and P from MG silicon, these methods are expensive, since the MG silicon starting material must be re-melted to above 1400° C. prior to purification, increasing the final silicon cost due factors such as energy, labor, capital equipment and yield losses.

It would be highly desirable and advantageous to either synthesize PV grade Si directly from high-purity starting materials, or use such high-purity starting materials to prepare Si that requires a minimum of post-synthesis purification prior to use in the manufacture of solar-cells. Attempts have been made to prepare PV grade silicon by beginning with high-purity natural quartz and carbon sources. However, the disadvantages of this method include the need to mine the quartz and crush it into smaller pieces prior to reduction to elemental silicon. These steps further increase the cost of the starting material and are a potential source of further impurity introduction. Also, the geological source of the quartz material may be a significant distance from the location of final silicon manufacture, further increasing costs due to transportation. Furthermore, quartz, being a crystalline form of $SiO_2$, is a known cause of the disease silicosis, which results when dust from such materials is inhaled.

There exist methods for isolating biogenic silica, that is, $SiO_2$ that is developed or assimilated in the cell structures of living organisms, from plants or parts of plants, such as rice hulls. These isolation methods typically involve burning the rice hulls and recovering the siliceous ashes for further use (Pitt, U.S. Pat. No. 3,889,608, and U.S. Pat. No. 3,959,007; Mehta, U.S. Pat. No. 4,105,459). However, this method of biogenic silica recovery tends to fuse or incorporate undesirable inorganic elements such as B and P into the silica during this high temperature processing, as well as reduce surface area of the silica due to pore collapse and closure. Furthermore, in many embodiments the silica derived from rice hulls is further refined by dissolving the silica in strong base, then precipitating it out of solution by the addition of acid (Stephens et. al, U.S. Pat. No. 6,375,735; U.S. Pat. No. 6,638,354; and U.S. Patent Application Publication US 2003/0097966; Kang, U.S. Pat. No. 6,843,974; Connor and Rieber, U.S. Pat. No. 5,078,795, U.S. Pat. No. 5,008,021; Rieber et al., U.S. Pat. No. 5,833,940; Shipley, U.S. Pat. No. 6,406,678).

Isolation of biogenic silica during the strong acid hydrolysis of rice straw has also been reported (Farone and Cuzens, U.S. Pat. No. 5,782,982). Sugars derived from this process are separated and purified prior to metabolic conversion into ethanol. The silica isolated from this strong acid hydrolysis process is dissolved using strong base, the supernatant liquid isolated and silica re-precipitated by lowering the pH of the supernatant liquid using acid. A major disadvantage of this methodology is the need to isolate the silica using strong bases and acids, which is very expensive due to the requirements of chemical storage, handling and disposal.

Biogenic silica derived from rice hulls has been used as a starting material for the preparation of silicon (Amick, U.S. Pat. No. 4,214,920). In these methods, rice hulls were typically first washed with water and/or dilute hydrochloric acid prior to being heated in either an inert or an oxygen atmosphere between 600° C. and 800° C. to carbonize or remove organic components, yielding a siliceous product that was then used to produce silicon. The chief disadvantage of these methodologies is the elimination or carbonization of organic materials such as cellulose from the rice hulls via simple burning, instead of isolating these materials and using them as feedstocks to create other economically valuable organic co-products. In addition, rice hulls, being very low density, are very expensive to transport, and any process utilizing rice hulls is consequently practically limited to a location close to rice-growing agricultural areas.

A second area of alternative energy production that has received significant attention is ethanol generation employing yeast fermentation of high-starch seeds from plants such as corn and wheat. However, there are significant problems with this method of ethanol production. For instance, this technology uses "food crops" and therefore competes with human and farm animal food supplies. Growing and harvesting of these crops is also "energy intensive" in terms of land preparation, the use of fertilizers and pesticides, irrigation requirements and the energy required to harvest and transport the crop materials to central processing locations. It has been estimated that it can take as much as 30 to 50 gallons of petroleum to produce one acre of corn for ethanol generation. In addition, there are concerns that agriculture techniques used to grow such crops may have long-term destructive effects such as soil erosion and water table contamination. Furthermore, there are limited ranges of suitable land where such crops can be cultivated. Also, the current art of utilizing grain crops such as corn to produce ethanol fuel is only economically viable through the generation of co-products, such as residual materials that may be sold for uses such as animal feed.

An alternative method of creating ethanol fuel from biomass involves the use of cellulose as a feedstock. There are currently two major methods of producing ethanol from such feedstocks: 1) a "Two-Step" process whereby the cellulose is broken down either enzymatically or chemically to glucose or cellobiose, followed by fermentation to ethanol by yeasts, and 2) a "One-Step" process whereby the cellulose is metabolized directly to ethanol under anaerobic conditions by cellulolytic thermophilic bacteria. One significant problem with current cellulose ethanol production is that many feedstocks (e.g., wood sources, grasses, etc.) contain a large percentage (as high as 30%) of lignin, a dense material which encapsulates the cellulose constituents, severely inhibiting or preventing access to this cellulose for breakdown into sugars by hydrolysis using enzymes or ethanol-producing microbes. Consequently, extensive pre-processing of cellulose-containing feedstocks such as wood is required to make the cellulose readily accessible to hydrolysis. Such pre-processing methods include mechanically reducing the size of the feedstock (e.g., converting wood to sawdust), harsh chemical treatments to separate the lignin from the cellulose, etc. These methods are highly energy intensive, can create significant amounts of chemical waste, and produce large quantities of lignin-based by-products, which have limited industrial value and are toxic.

There is accordingly a need for additional methods for producing silica and ethanol from plant material, which overcome at least some of the disadvantages associated with prior art methods.

SUMMARY OF THE INVENTION

According to one aspect of the invention, there is provided a method for the co-production of silica and at least one other useful industrial chemical product, comprising the steps of:
a) pre-treating siliceous plant matter to create a feedstock having exposed cellulose;
b) placing the feedstock in a reactor containing a biological agent effective to break down the cellulose into at least one useful organic chemical reaction product and a silica-containing co-product;
c) separating the at least one useful organic chemical product from the reactor;
d) separating the silica-containing co-product from the reactor; and
e) refining the silica-containing co-product into silica or other industrially useful silicon-containing products.

The siliceous plant matter may be derived from the members of the genus *Equisetum*, and the useful organic chemical reaction product may be selected from the group comprising ethanol, methane, hydrogen and acetates. The biological agent may comprise a culture or co-culture of anaerobic thermophyllic bacteria, enzymes, or a co-mixture of enzymes and yeast. In a preferred embodiment of the invention, the siliceous plant matter is derived from plants of the genus *Equisetum*, the biological agent is a thermophyllic anaerobic bacteria, and the useful organic chemical reaction product is ethanol.

According to another aspect of the invention, there is provided a method for the co-production of silica and ethanol, comprising the steps of:
a) pre-treating siliceous plant matter derived from plants of the genus *Equisetum* to create a feedstock having exposed cellulose;
b) placing the feedstock in a chemicobiological reactor containing a biological agent effective to break down the cellulose into ethanol and a silica-containing co-product;
c) separating the ethanol from the reactor;
d) separating the silica-containing co-product from the reactor; and
e) refining the silica-containing co-product into silica or other industrially useful silicon-containing products.

BRIEF DESCRIPTION OF THE DRAWINGS

For a better understanding of the embodiments, and to show more clearly how they may be carried into effect, reference will now be made, by way of example, to the accompanying drawings, in which.

DETAILED DESCRIPTION OF VARIOUS EMBODIMENTS

Figure 1:
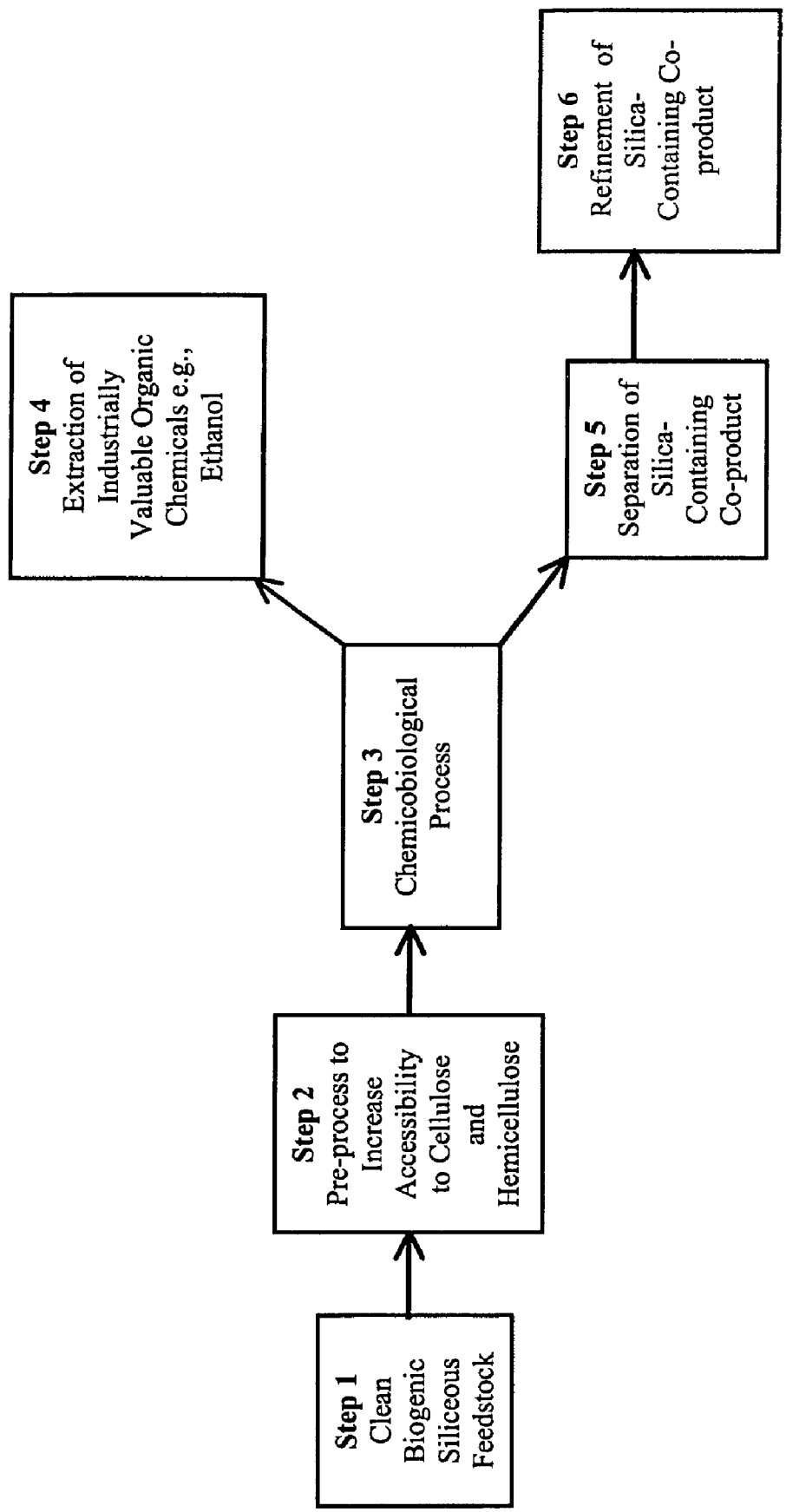
FIG. 1 is a block diagram illustrating a method in accordance with an embodiment of the invention.

The present invention is directed to methods for the co-production of both high-purity silica, which is suitable for applications such as the synthesis of silicon for solar-cells, silicon tetrachloride and silicon carbide, and industrially useful chemicals such as ethanol, using a biological process that breaks down the cellulose found in siliceous plant material from plants such as *Equisetum*.

The present inventor has determined that plants in the genus *Equisetum*, known as "horsetail weeds", are a preferred type of siliceous plant material for use with the method of the present invention, for a number of reasons. *Equisetum* plants contain some of the highest biogenic silica content known in the plant kingdom, at times in excess of 15% dry weight. Silica, isolated from such plants in high purity form will have many highly advantageous properties if it is used as an $SiO_2$ source in the carbothermic generation of silicon. For instance, silica derived from *Equisetum* is amorphous, and therefore should not cause silicosis. In addition, *Equisetum* silica has a fine particulate, open-porous structure. These properties are advantageous since small particles with open structure will facilitate further purification of the silica after isolation by methods such as rinsing, etc. Furthermore, these physical properties will also facilitate reaction of the $SiO_2$ with carbon due to the close proximity and high surface area of the $SiO_2$ starting material.

In addition to having some of the highest levels of biogenic silica in the plant world, one common member of the genus *Equisetum* contains cellulose that is significantly less polymerized (e.g., likely more easily broken down into glucose and cellobiose) than cellulose found in typical plants. Perhaps more significantly, several common species of *Equisetum* are very low in lignin content, which is highly desirable in a cellulose ethanol feedstock. For instance, one species of *Equisetum* has as little as half the lignin content of other proposed cellulosic ethanol feedstocks such as poplar and switchgrass. Also, a very common species of *Equisetum* is low in 5-carbon sugars, which are difficult to microbiologically convert into ethanol. Unlike rice, which must be cultivated and has a limited range of habitats in which it grows, *Equisetum* is a rhizome and tuber-based self replicating perennial plant that grows naturally and prolifically in non-agricultural land from the tropics to north of the arctic circle. One common species of horsetail weed, *Equisetum arvense*, readily decomposes in nature indicative of easy microbial digestion of this biomass source.

Referring now to FIG. 1, the first step of a method according to an embodiment of the invention (Step 1) is to clean the biogenic siliceous feedstock to remove material that is not desirable in further steps. Such material may include dirt, stones, sand and other extraneous material such as undesirable plant matter, etc. This step may include washing with water and/or other cleaning agents that are commonly employed in the art.

Step 2 of the subject method is to pre-process the biogenic siliceous feedstock material to render the sugar-containing polymers such as cellulose and hemicellulose in the feedstock more accessible and or chemically processable to further processing steps as well as aid in the removal of undesirable material such as unwanted metal ions, lignin, etc. These methods may include but are not limited to mechanical processing to reduce the physical size of the biogenic silicate feedstock material. Such methods may include chopping, cutting, shredding, grinding, pureeing, crushing, and ultrasonic dispersal. Chemical and or physiochemical methods commonly employed in the art may also be used such as pulping, water rinsing, steam treatment at or above atmospheric pressure, freezing, solvent pre-treatment, treatment with acid or base solutions for the purposes of freeing up sugars from the matrix via hydrolysis, as well at treatment of the substrate with oxygenating agents. Electromagnetic methods may also be used to pre-treat the feedstock, including heat, light including ultraviolet and microwave energy. The feedstock may also be treated with ultrasound. In addition, the biogenic feedstock may be pre-treated with biological agents such as mold and fungi.

In Step 3 of the subject method, the pre-processed biogenic siliceous feedstock is added to a chemicobiological reactor containing a biological agent that is effective to break down sugar-based polymers such as cellulose and hemicellulose contained within the feedstock and convert them into industrially valuable chemicals such as ethanol, which may be subsequently recovered from the reactor. For the purposes of this document, the term chemicobiological is used to refer to processes involving either metabolism by living cells such as yeast or bacteria, or chemical processing employing biologically derived or synthetic analogs of chemicals found in metabolic processes, such as enzymes.

Step 3 of the subject method also produces a silica-containing co-product having an organic content that is less than that of the feedstock, which can be more easily refined into silica and other useful silicon-containing products, after isolation. The silica-containing co-product may include silica mixed with lignin and other carbon containing organic material.

In one embodiment of the subject method, the biological agent employed in the reactor is an ethanol producing anaerobic bacteria, either in single strains or mixed co-cultures. In a preferred embodiment, the anaerobic bacteria comprises a thermophyllic bacteria such as *Clostridium thermocellum*, *Clostridium thermodydrosulfuricum* and *Thermoanaerobacter ethanolicus*. There are many advantages to cellulosic ethanol production employing anaerobic thermophylic bacteria. For instance, the elevated temperatures that are optimum for these bacteria (e.g., 66° C. to 69° C.) also favor low oxygen solubility, low medium viscosity, high metabolic rates, and simple and continuous extraction of the valuable organic chemical ethanol from the reaction media using mild vacuum or inert gas steam methodologies.

It should be understood, however, that the chemicobiological process of the subject method is not limited to the use of anaerobic bacteria and co-cultures, and may utilize other biological agents and other bioorganic processes. For instance, in another embodiment, the chemicobiological reactor may contain a co-mixture of enzymes that break down the polysaccharides cellulose and hemicellulose in the biogenic siliceous feedstock into compounds such as cellobiose, 5- and 6-carbon sugars, etc., which may be further metabolized in this reactor into industrially useful chemicals such as ethanol by microbes such as yeasts. In yet another embodiment, the reactor may contain enzymes such as those derived from species such as the anaerobic fungus *Trichhoderma reesi*. These enzymes can be employed to produce industrially valuable compounds such as cellobiose, 5- and 6-carbon sugars, etc. from cellulose and hemicellulose, which may be isolated for further use, such as fermentation by yeast into ethanol. Still other biological agents that may be employed in the reactor include organisms such as fungi and molds. Furthermore, other industrially useful chemicals besides ethanol produced within the reactor may be extracted, such as acetates, hydrogen, methane, etc. Also, it is understood by those familiar with the art that the process described in Step 3 may be a continuous or batch process. In addition, the isolation of the valuable organic products produced by the chemicobiological reaction may necessitate further processing, such as distillation of the reaction solution, recrystallization, etc.

Step 4 of the subject method involves the separation and recovery of the ethanol or other useful chemical product from the chemicobiological reactor. This can by accomplished by a separation processes that are well known in the art, such as distillation or removal by continuous flow of inert gas over the reaction solution.

Step 5 of the subject method involves the separation and recovery of the silica-containing co-product from the chemicobiological reactor. This may be accomplished by common means known to those who are familiar with the art, means such as but not limited to precipitation, filtration, centrifugation, flocculation, belt pressing, etc.

Step 6 of the subject method involves refining the silica-containing co-product into silica or other industrially useful silicon-containing products. Such refining may include the removal of any organic materials that are associated with the silica-containing co-product, removal of unwanted inorganic constituents such as metal ions, etc. Methods may include rinsing, preferably with high-purity reagents such as deionized water, at or above room temperature and pressure, with or without chelating agents to aid in the removal of unwanted ions, acidic or basic solutions, and or solvents. Other treatments may include electromagnetic irradiation and treatment with oxygenating agents such as hydrogen peroxide and ozone at room temperature or at elevated temperature. Further refinement may involve the use of chemicobiological agents such as bacteria, yeasts, fungi, molds and enzymes. The isolated silica may be dried by means common in the art such as baking in oxygen, air, or under inert gas or under vacuum conditions.

It should be understood, however, that in some cases, the retention of organic components recovered with the silica-containing co-product may be desirable. For instance, a silica-containing co-product consisting of finely mixed lignin or other carbon-containing organic material may be thermally processed under an inert atmosphere such as nitrogen or argon for the purposes of converting the carbon-containing components into elemental carbon. Such processing will render the silica-containing co-product into a form that may be used as a chemical precursor for the formation of final products such as silicon or silicon tetrachloride. The atmosphere used for pyrolysis may also contain reactive gases such as HCl for the purposes of removing undesirable inorganic elements contained within the silica-containing co-product.

In one embodiment, the step of refining the silica-containing co-product comprises a process for recovering high purity silica that is finely mixed with elemental carbon, which is a desirable product for further conversion into useful materials such as silicon, silicon tetrachloride or silicon carbide. Such process may comprise the steps of rinsing the silica-containing co-product with water, acids or solvent, heating the silica containing product under an inert atmosphere containing anhydrous HCl at a temperature between 400° C. and 1600° C. for the purposes of converting any residual organic materials to elemental carbon and further removing any unwanted inorganic elements, so as to produce silica mixed with elemental carbon.

In another embodiment, the step of refining the silica-containing co-product comprises a process for recovering high purity silica by itself. This process may comprise the steps of dissolving the silica in the silica-containing co-product in strong base, separating the supernatant liquid by methods such as filtering, re-precipitating the silica using acid, isolating the silica by methods such as filtration, heating the isolated silica under an inert atmosphere containing anhydrous HCl at a temperature between 400° C. and 1600° C., treating the silica with aqueous oxidants including hydrogen peroxide and ozone, and heating under an oxidizing atmosphere to remove any remaining organics at a temperature between 300° C. and 1600° C.

In a further embodiment, the step of refining the silica-containing co-product comprises the steps of rinsing the silica-containing co-product with water, acids or solvent, treating the carbon-containing silicate with aqueous oxidants including hydrogen peroxide and ozone, and heating under an oxidizing atmosphere to remove organics at a temperature between 300° C. and 1600° C., thereby producing a high purity silica.

The method of the present invention may include the step of further refining the silica or other useful silicon-containing products. For example, the carbon content of the isolated silica may be adjusted through means such as blending the silica with a carbon rich source such as sugar, starch or molasses, and heating this mixture under an inert atmosphere that may contain a reactive gas such as HCl for the purposes of converting the organic constituents into elemental carbon. This carbon-containing silica may be further processed, such as adjusting the carbon content of the silica by heating the silica under an atmosphere of argon and carbon dioxide. This carbon containing silica may be used for processes such as a feedstock for the preparation of high-purity elemental silicon.

One significant advantage of method of the subject invention is that the method does not involve the burning of the siliceous plant material. If the *Equisetum* were to be simply burned, the resulting silica-rich ash would contain undesirable concentrations of elements such as P, B, Na, K, Mg, Ca, Fe, etc., which are known to degrade the photovoltaic properties of silicon. However, many ethanol-producing anaerobic thermophylic bacteria require a large variety of inorganic ions and compounds as nutrients to live and grow. Such inorganic nutrients include phosphates, borates, as well as inorganic salts of Na, K, Mg, Ca, Fe, etc. In the process of metabolizing the silica containing feedstock, it believed that the ethanol-producing microbes such as anaerobic thermophyllic bacteria will extract unwanted inorganic ions from the feedstock material, leaving a higher purity silica than could be obtained by methods such as simple burning.

As noted above, the isolated silica may be used for the generation of other silicon containing industrially valuable chemicals aside from elemental silicon. For example, the silica and carbon mixture may be heated in the presence of carbon to produce silicon carbide (SiC), or a halide such as chlorine to produce industrially valuable chemicals such as silicon tetrachloride ($SiCl_4$).

What has been described is merely illustrative of the application of some embodiments of the invention. Other methods may be implemented by those skilled in the art without departing from the present invention, the scope of which is defined by the following claims. In particular, various methods described above provide an example of one or more embodiment of any claimed inventions. No embodiment described limits any claimed invention and any claimed invention may cover methods that are not described above. The claimed inventions are not limited to methods having all of the features of any one method described above or to features common to multiple or all of the methods described above. It is possible that methods described above are not an embodiment of any claimed invention. The applicants, inventors or owners reserve all rights that they may have in any invention disclosed in methods described above that is not claimed in this document, for example the right to claim such an invention in a continuing or divisional application and do not intend to abandon, disclaim or dedicate to the public any such invention by its disclosure in this document.

The invention claimed is:

1. A method for the co-production of silica and at least one other useful industrial chemical product, comprising the steps of:
   a) pre-treating siliceous plant matter to create a feedstock having exposed cellulose, wherein the siliceous plant matter is derived from members of the genus *Equisetum*;
   b) placing the feedstock in a reactor containing a biological agent effective to break down the cellulose into at least one useful organic chemical reaction product and a silica-containing co-product, wherein the biological agent comprises a culture of anaerobic thermophyllic bacteria, and wherein the useful organic chemical reaction product is selected from the group comprising ethanol, methane and hydrogen;
   c) separating the at least one useful organic chemical product from the reactor;
   d) separating the silica-containing co-product from the reactor; and
   e) refining the silica-containing co-product into silica or other industrially useful silicon-containing products.

2. The method defined in claim 1, wherein the step of pre-treating the siliceous plant material comprises a pretreatment step selected from a group consisting of chopping, crushing, shredding, pureeing, grinding, water soaking with or without surfactants, heat treatment in the presence or absence of chemicals below, at or above atmospheric pressure, microwave exposure, ultrasound, and treatment with biological agents such as mold and fungi.

3. The method defined in claim 1, wherein the step of separating the useful organic chemical reaction product comprises a separation process selected from a group consisting of distillation below, at or above atmospheric pressure, and removal by continuous flow of inert gas over the reaction solution.

4. The method defined in claim 1, wherein step of separating the silica-containing co-product comprises a separation process selected from a group consisting of precipitation, filtration, centrifugation, flocculation and belt-pressing.

5. A method for the co-production of silica and at least one other useful industrial chemical product, comprising the steps of:
   a) pre-treating siliceous plant matter to create a feedstock having exposed cellulose;
   b) placing the feedstock in a reactor containing a biological agent effective to break down the cellulose into at least one useful organic chemical reaction product and a silica-containing co-product;
   c) separating the at least one useful organic chemical product from the reactor;
   d) separating the silica-containing co-product from the reactor; and
   e) refining the silica-containing co-product into silica or other industrially useful silicon-containing products;
   f) wherein the step of refining the silica-containing co-product comprises the steps of rinsing the silica-containing co-product with water, acids or solvent, heating the silica-containing co-product under an inert atmosphere containing anhydrous HCl at a temperature between 400.degree. C. and 1600.degree. C. for the purposes of converting any residual organic materials to elemental carbon and further removing any unwanted inorganic elements, so as to produce a high purity silica mixed with elemental carbon.

6. A method for the co-production of silica and at least one other useful industrial chemical product, comprising the steps of:
   a) pre-treating siliceous plant matter to create a feedstock having exposed cellulose;
   b) placing the feedstock in a reactor containing a biological agent effective to break down the cellulose into at least one useful organic chemical reaction product and a silica-containing co-product;
   c) separating the at least one useful organic chemical product from the reactor;
   d) separating the silica-containing co-product from the reactor; and
   e) refining the silica-containing co-product into silica or other industrially useful silicon-containing products;
   f) wherein the step of refining the silica-containing co-product comprises the steps of dissolving silica in the silica-containing co-product in a strong base leaving a carbon component of the silica-containing siliceous product undissolved, filtering the supernatant liquid, precipitating the silica from the supernatant liquid by adding an acid, isolating the silica, heating the silica product under an inert atmosphere containing anhydrous HCl at a temperature between 400.degree. C. and 1600.degree. C., treating the silica with aqueous oxidants including hydrogen peroxide and ozone, and heating the silica under an oxidizing atmosphere to remove organics at a temperature between 300.degree. C. and 1600.degree. C., thereby producing a high purity silica.

7. The method defined in claim 1, wherein the step of refining the silica-containing co-product comprises the steps of rinsing the silica-containing co-product with water, acids or solvent, treating the carbon-containing silicate with aqueous oxidants including hydrogen peroxide and ozone, and heating under an oxidizing atmosphere to remove organics at a temperature between 300.degree. C. and 1600.degree. C., thereby producing a high purity silica.

8. The method defined in claim 5, wherein the step of refining the silica-containing co-product comprises the further steps of blending the high purity silica with a carbon source, converting the carbon source to elemental carbon at a precise ratio by heating the silica under a controlled atmosphere, then processing the carbon-containing silica to create the industrially useful silicon-containing products.

9. The method defined in claim 1, wherein the industrially useful silicon-containing products include elemental silicon, silicon tetrachloride and silicon carbide.

10. A method for the co-production of amorphous silica and ethanol, comprising the steps of:
    a) pre-treating siliceous plant matter derived from plants of the genus *Equisetum* to create a feedstock having exposed cellulose and hemicellulose;
    b) placing the feedstock in a chemicobiological reactor containing a biological agent, effective to break down the cellulose into ethanol and a silica-containing co-product, wherein the biological agent comprises a culture of anaerobic thermophyllic bacteria;
    c) separating the ethanol from the reactor;
    d) separating the silica-containing co-product from the reactor; and
    e) refining the silica-containing co-product into silica or other industrially useful silicon-containing products.

11. The method defined in claim 10, wherein the step of separating the ethanol from the reaction solution comprises distillation below, at or above atmospheric pressure.

12. The method defined in claim 10, wherein step of separating the silica-containing co-product comprises a process selected from a group consisting of precipitation, filtration, centrifugation, flocculation and belt-pressing.

13. The method defined in claim 5, wherein the siliceous plant matter is derived from members of the genus *Equisetum*.

14. The method defined in claim 13, wherein the useful organic chemical reaction product is selected from the group comprising ethanol, methane, hydrogen and acetates.

15. The method defined in claim 14, wherein the biological agent comprises a cultural of an anaerobic thermophyllic bacteria.

16. The method of claim 5, wherein the biological agent comprises a co-mixture of enzymes and yeast.

17. The method defined in claim 5, wherein the biological agent comprises enzymes affective to break down the cellulose into constituent sugars.

18. The method defined in claim 6, wherein the siliceous plant matter is derived from members of the genus *Equisetum*.

19. The method defined in claim 18, wherein the useful organic chemical reaction product is selected from the group comprising ethanol, methane, hydrogen and acetates.

20. The method defined in claim 19, wherein the biological agent comprises a cultural of an anaerobic thermophyllic bacteria.

21. The method of claim 6, wherein the biological agent comprises a co-mixture of enzymes and yeast.

22. The method defined in claim 6, wherein the biological agent comprises enzymes affective to break down the cellulose into constituent sugars.

* * * * *

UNITED STATES PATENT AND TRADEMARK OFFICE
CERTIFICATE OF CORRECTION

| | | |
|---|---|---|
| PATENT NO. | : 8,026,086 B2 | Page 1 of 1 |
| APPLICATION NO. | : 12/051925 | |
| DATED | : September 27, 2011 | |
| INVENTOR(S) | : Anthony A. Rywak | |

It is certified that error appears in the above-identified patent and that said Letters Patent is hereby corrected as shown below:

Title Page, item (73), Assignee: REPLACE "Ontario Inc." with "1695492 Ontario Inc. d.b.a. Global-Meridian Technology Group"

Signed and Sealed this
Fourteenth Day of February, 2012

David J. Kappos
*Director of the United States Patent and Trademark Office*